(12) United States Patent
Conchy et al.

(10) Patent No.: US 6,749,613 B1
(45) Date of Patent: Jun. 15, 2004

(54) DISTRACTION/CONTRACTION DEVICE FOR SPINAL OSTEOSYNTHESIS SYSTEM

(75) Inventors: Frédéric Conchy, Saint-Médard d'Eryans (FR); Denis Pasquet, Bordeaux (FR)

(73) Assignee: Stryker Spine (FR)

( * ) Notice: Subject to any disclaimer, the term of this patent is extended or adjusted under 35 U.S.C. 154(b) by 0 days.

(21) Appl. No.: 09/913,692

(22) PCT Filed: Feb. 18, 2000

(86) PCT No.: PCT/FR00/00414

§ 371 (c)(1),
(2), (4) Date: Dec. 10, 2001

(87) PCT Pub. No.: WO00/48523

PCT Pub. Date: Aug. 24, 2000

(30) Foreign Application Priority Data

Feb. 18, 1999 (FR) .............................. 99 01987

(51) Int. Cl.[7] .............................. A61B 17/56
(52) U.S. Cl. .......................... 606/61; 606/57
(58) Field of Search .............................. 606/53–58, 61, 606/63, 68–72, 73

(56) References Cited

U.S. PATENT DOCUMENTS

| 4,926,849 A | | 5/1990 | Downey | |
|---|---|---|---|---|
| 5,393,036 A | * | 2/1995 | Sheridan | 254/100 |
| 6,126,660 A | * | 10/2000 | Dietz | 606/61 |
| 6,241,731 B1 | * | 6/2001 | Fiz | 606/65 |
| 2003/0167059 A1 | * | 9/2003 | Young | 606/61 |

FOREIGN PATENT DOCUMENTS

| DE | 40 07 306 C1 | 5/1991 |
|---|---|---|
| DE | 91 12 466.2 | 1/1992 |
| WO | WO-93/14908 A | 8/1993 |

OTHER PUBLICATIONS

Database WPI Section PQ, Week 8650 Derwent Publications Ltd., London, GB: Class P31, AN 1986–330695 XP002120733 & SU 1 223 904 A (Mosc Reg Clinic Ins) abstract: figures.

* cited by examiner

Primary Examiner—Pedro Philogene
Assistant Examiner—David A Bonderer
(74) Attorney, Agent, or Firm—Lerner, David, Littenberg, Krumholz & Mentlik, LLP (57) ABSTRACT

The invention concerns a distraction and/or contraction device for backbone surgery comprising connectors designed to be fixed to respective vertebral anchoring members, linkup means between said connectors and means for adjusting the distance between said connectors including a pinion assembly and an endless screw.

46 Claims, 7 Drawing Sheets

FIG_1

FIG_2

DISTRACTION/CONTRACTION DEVICE FOR SPINAL OSTEOSYNTHESIS SYSTEM

The present invention relates to instrumentation for spinal osteosynthesis systems.

When fitting a spinal osteosynthesis system in place, the surgeon is forced to modify the distance separating the two vertebrae receiving the osteosynthesis system. Moreover, when fitting this by an endoscopic route, the use of a conventional forceps called a distractor (used in cases where the vertebrae are to be spaced apart from one another) or called a contractor (used in cases where the vertebrae are to be brought closer to one another) is problematic or even impossible on account of its size. Furthermore, the endoscopy instruments have courses which are too short or they do not permit the application of sufficient forces to perform the operation of distraction or contraction.

Furthermore, the document DE 91 12 466 U discloses instrumentation with which it is possible to position two pedicle screws relative to one another. This instrumentation is made up of two arms interfacing with the pedicle screws and linked to each other by two displacement devices which each have two threads in opposite directions and engaging with the respective arms. The instrumentation as a whole is very voluminous, which means that it cannot be used in endoscopic surgery.

It is an object of the present invention to make available a device which permits distraction and contraction of two vertebrae while at the same time being able to be applied by an endoscopic route and being easy to use.

According to the present invention, this object is achieved by providing a distraction and/or contraction device for surgery of the spine, comprising connectors designed to be fixed to respective vertebral anchoring members, means for linking these connectors, and means for adjusting a distance comprising an assembly of pinion and endless screw.

Thus, the device makes it possible to perform distraction or contraction between two vertebrae in a simple way, while maintaining the applied displacement by a nonreturn effect without any intervention by the operating surgeon.

Advantageously, the means for adjusting a distance comprise a rod designed to link the connectors.

Advantageously, the rod is free both in translation and rotation on its own axis relative to one of the connectors.

Advantageously, the rod is free in rotation about its own axis relative to the other of the connectors.

Advantageously, the rod is free both in translation and rotation on its own axis relative to the other of the connectors with a helix of opposite direction.

Advantageously, the rod is immobilized in translation and in rotation on its own axis relative to one of the connectors.

Advantageously, the rod is free in translation on its own axis relative to the other of the connectors.

Advantageously, the pinion is rigidly integral with the rod.

Advantageously, the pinion forms a screw/nut link with the rod.

Advantageously, the device comprises linking means between the rod and the connectors, these linking means comprising the pinion.

Advantageously, the device comprises linking means between the rod and the connectors, these linking means comprising a block which forms an abutment for the translation and/or rotation movement of the rod relative to the connector on the axis of the rod.

Advantageously, the block has a polygonal cross section, preferably with four sides.

Advantageously, at least one of the connectors has a bifid hook delimiting a space designed to receive the rod and its means of linkage.

Thus, the device can be dismantled into small elements, thus facilitating its use by endoscopy and also its assembly.

Advantageously, the device is designed in such a way that when the block is received, one of the sides of the polygonal cross section of the abutment is able to come into contact with the bottom of the space of the bifid hook.

Advantageously, one of the connectors comprises a ring with a spherical face.

Advantageously, the connector comprises a chamber designed to receive the ring with rotation.

Advantageously, the connector comprises a locking means designed to immobilize the ring in rotation.

Advantageously, the locking means comprises a concave spherical face designed to come into contact with the spherical face of the ring.

Advantageously, one of the connectors is adjacent to the pinion and endless screw assembly.

Advantageously, the endless screw can be received with rotation in the connector.

Advantageously, the device additionally comprises an instrument, for maneuvering the endless screw, and designed to receive the endless screw with rotation.

Advantageously, the instrument comprises a bifid hook delimiting a space, designed to receive the rod and the pinion rigidly integral with the rod.

The invention also provides a spinal osteosynthesis system comprising two vertebral anchoring members and a distraction and/or contraction device according to the present invention.

Advantageously, one of the connectors is able to form a ball and socket link with the associated vertebral anchoring member.

Thus, the device can be placed on anchoring members with defective alignment and parallelism.

Advantageously, the ring is designed to be fitted on the vertebral anchoring member.

The invention also provides a surgical method intended to perform spinal osteosynthesis with the aid of such an osteosynthesis system comprising a distraction and/or contraction device according to the present invention: placing the anchoring members on the vertebrae, then placing the device on the anchoring members and adjusting the distance, then fitting the osteosynthesis system, then removing the device.

Other characteristics and advantages of the invention will become clearer from the following description of three preferred embodiments which are given as nonlimiting examples. In the attached drawings.

We will now describe a first embodiment of the present invention shown in FIGS. 1 to 5.

Figure 1:
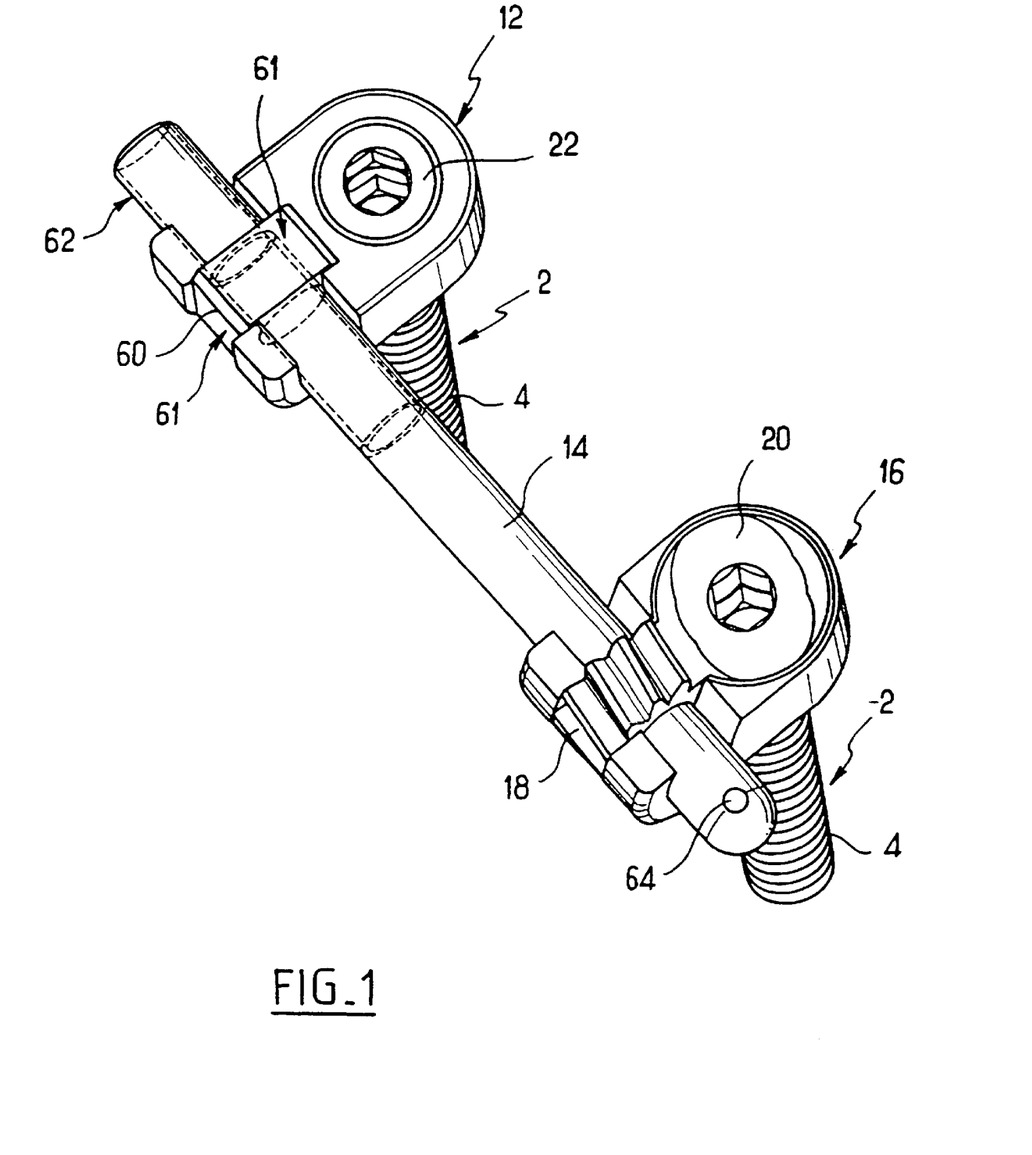
FIG. 1 is a view, in three dimensions, of a first preferred embodiment.
Figure 2:
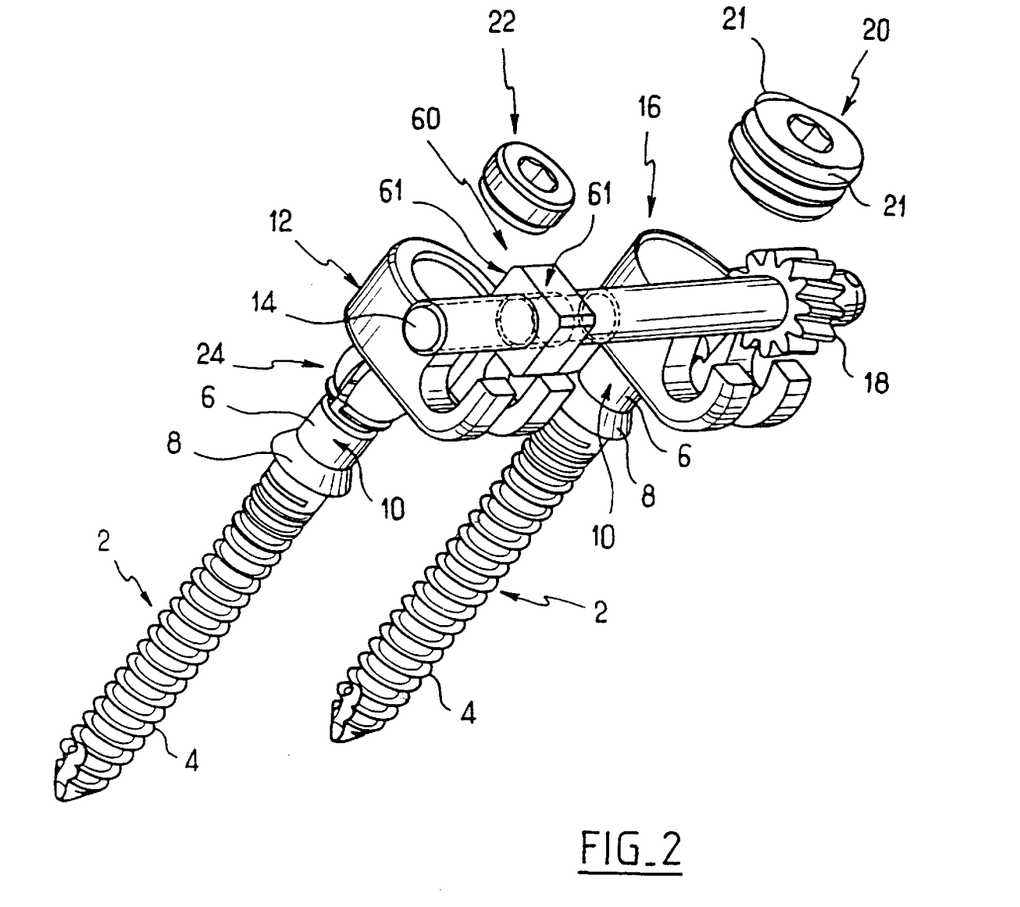
FIG. 2 is an exploded view of the first embodiment.

The spinal osteosynthesis system comprises vertebral anchoring members, here in the form of bicortical screws 2, each having a threaded body 4 and a cylindrical head 6 surmounting a flange 8. The cylindrical head 6 has a smooth outer face 10 forming a cylinder with axis that of the bicortical screw 2.

For each pair of bicortical screws 2 situated on a vertebral body 100, 200, the device comprises a first connector 12, a rod 14, a second connector 16, and drive means 18 and 20.

Figures 3A, 3C:
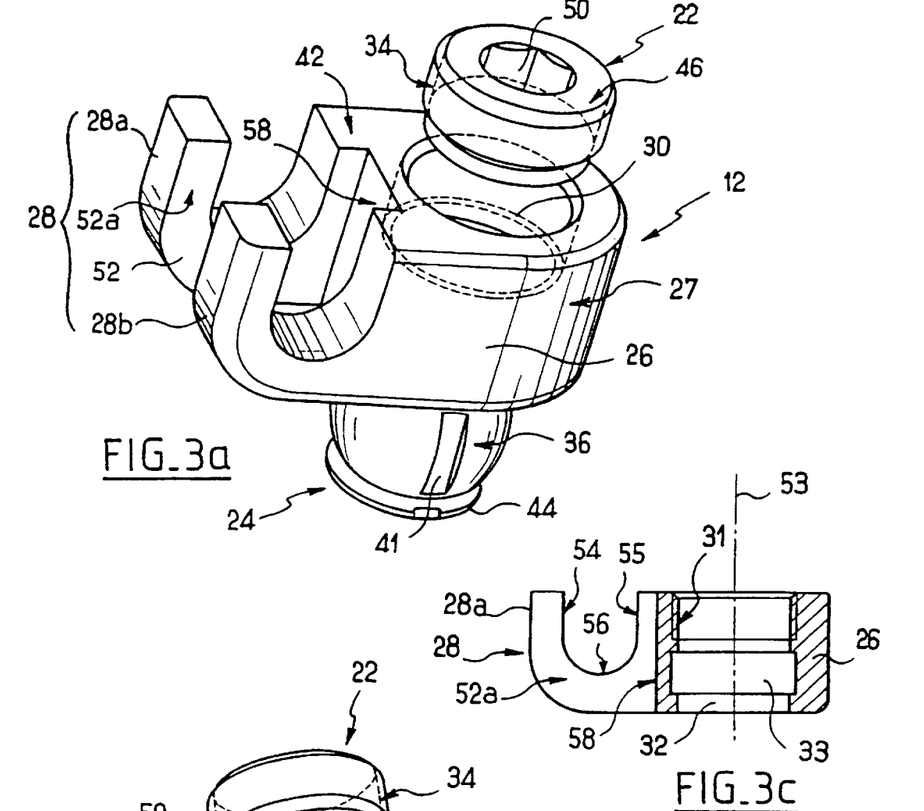
FIGS. 3a and 3b are exploded views of the first connector, in three dimensions, and at two different angles.
FIG. 3c is an axial section through the first connector.
Figure 3B:
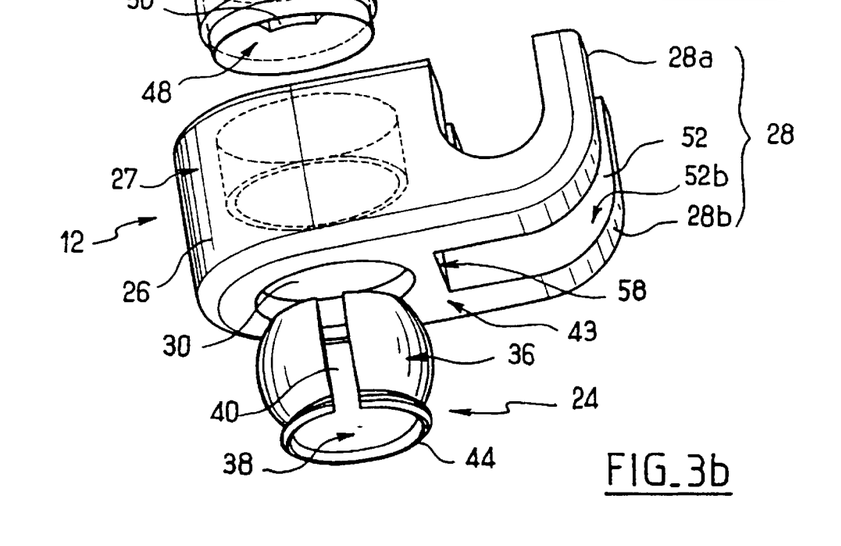

The first connector 12 is made up of a body 26 and of a receiving hook 28.

The body 26 is of generally parallelepipedal shape with a cylindrical rear face 27 of semicircular cross section and with a diameter equal to the side of the parallelepiped. Passing through the body 26 from its upper face 42 to its lower face 43 there is a cylindrical orifice 30 of circular cross section consisting of an upper part 31 and a lower part 32. The upper part 31 is a tapped hole whose thread is complementary with the thread 34 of a locking means 22, allowing the latter to engage in the orifice 30. The lower part 32 comprises a smooth hole with a seat 33 formed by a recess of circular cross section coaxial with the orifice 30, making it possible to receive and firmly secure a ring or a collar 24.

The collar 24 has a smooth outer face 36 of spherical shape with the same radius as that of said recess 33, and a smooth inner face 38, of somewhat cylindrical shape, having the same diameter as the smooth outer face 10 of the bicortical screw 2. The collar 24 comprises a slit 40 running straight from the outer face 36 to the inner face 38 along the whole length of the collar 24. It additionally comprises a groove 41 set diametrically opposite the slit 40 and situated on the outer face 36. A retaining lip 44 protrudes from the lower face of the collar 24. This lip 44 ensures that the opening of the orifice delimited by the inner face 38 of the collar 24 is not obstructed by the rotation of said collar 24 in its seat 33, which would prevent the connector 12 from being mounted on the head of the bicortical screw 2.

The locking means 22 comprises a plane upper face 46 and a concave hemispherical lower face 48 substantially of the same diameter as the spherical face 36 of the collar 24 and covering the latter upon assembly. A hexagonal indent 50 starts from the upper face 46 and opens out on the lower face 48, permitting fitting of a drive means for moving the locking means 22 with a view to screwing it or unscrewing it.

The receiving hook 28 is bifid. It is made up of two U-shaped hooks 28a, 28b which are separated by a space 52. The branches of the "U" are parallel to each other and parallel to the axis 53 of the orifice 30. The bottom 56 of the hooks is circular for receiving the rod 14 during use of the device. The space 52 is delimited by a bearing face 58 parallel to the axis 53 of the orifice 30, on the one hand, and, on the other hand, of the circular bottom 56 of the hooks 28a, 28b. The space 52 is also delimited by the faces 52a and 52b forming the sides of the respective hooks 28a and 28b. Thus, the space 52 is configured in such a way as to permit the insertion of a block 60 of square cross section, of which one of the sides 61 is in contact with the bearing face 58, thus immobilizing the block 60 in rotation. The faces 52a and 52b for their part cancel translation movements on the axis of the receiving hook.

In this preferred embodiment, the rod 14 has a thread 62 which engages with the thread of the block 60, the latter then serving as a nut, screwing and unscrewing depending on the movements of the rod 14. At the other end of the rod 14, a grip orifice 64 precedes a pinion 18 which is integral with the rod 14. The grip orifice 64 allows the rod 14 to be manipulated during an endoscopy procedure. The drive means include, in addition to the pinion 18, an endless screw 20. The endless screw 20 comprises at least one drive thread 21.

The pinion 18 is helicoidal with a helix angle corresponding to the slope of the drive threads 21 of the endless screw 20 (angle of between 5° and 25°).

Starting from the upper face 66 of the endless screw 60 there is a hexagonal indent 68 which permits fitting of a drive means. This indent 68 opens out in a circular chamber 70 which extends as far as the lower face 72 of the endless screw 20. This circular chamber 70 has a diameter corresponding to the diameter of the outer face 10 of the head 6 of the bicortical screw 2, so that the latter can lodge there without difficulty and without disturbing the rotational movement of the endless screw 20. The axis of the indent 68 and the axis of the circular chamber 70 coincide with the axis 67 of the endless screw 20.

Figures 4A, 4B, 4C:
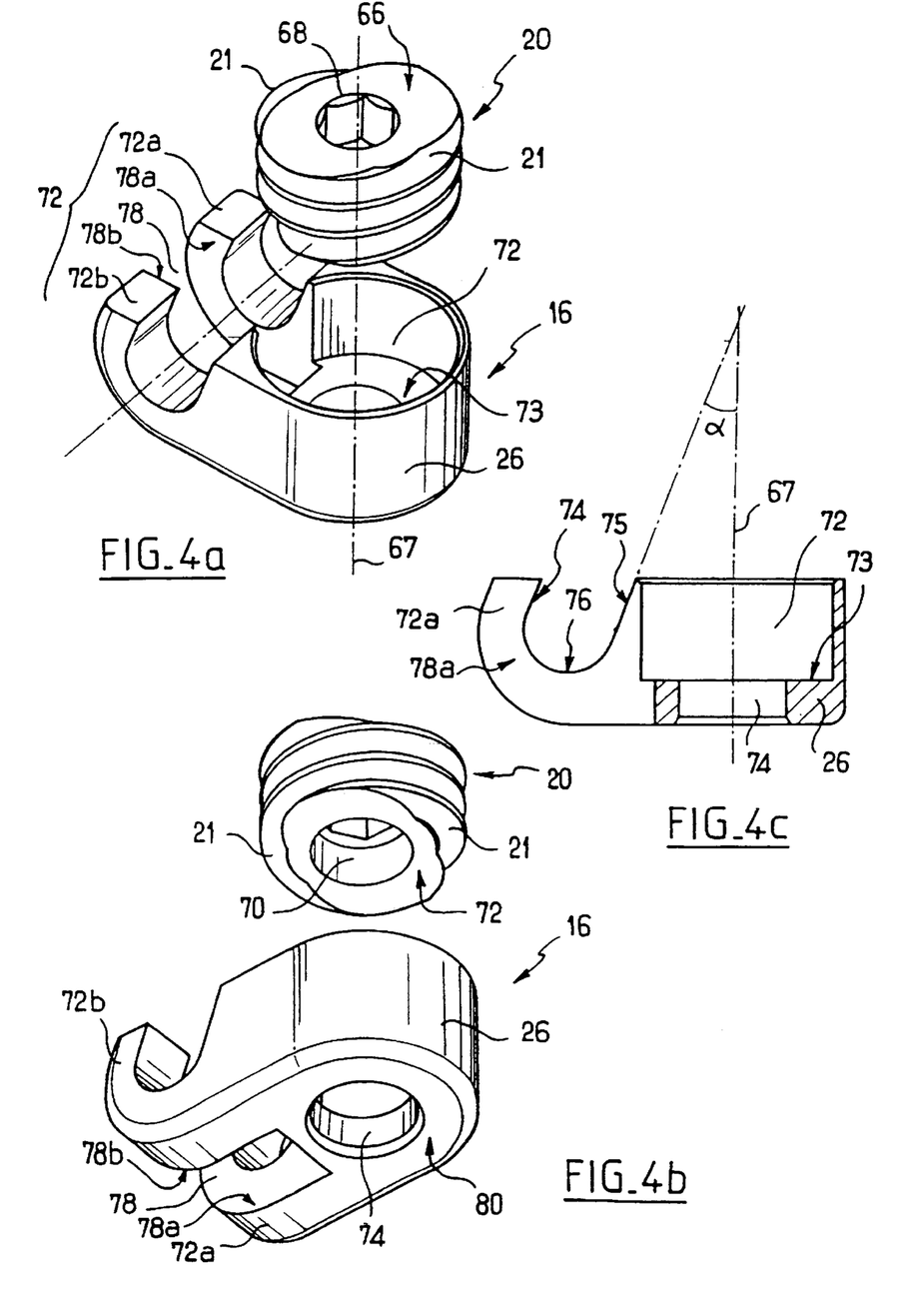
FIGS. 4a and 4b are exploded views of the second connector, in three dimensions, and at two different angles.
FIG. 4c is an axial section through the second connector.

The second connector 16 differs from the first connector 12 in that it comprises:

Instead of the orifice 30 of the body 26, a circular chamber 72 which can receive the endless screw 20: its diameter is slightly greater than that of the endless screw 20 and its depth is equal to the height of the endless screw 20. From the bottom 73 of this receiving chamber 72, a coaxial hole 74 is formed in such a way as to open out on the lower face 80 of the second connector 16. The diameter of this hole 74 is identical to that of the circular chamber 70 of the endless screw 20 with a view to permitting the passage of the head 6 of the bicortical screw 2.

A bifid receiving hook 72, of which the branches 74, 75 of the "U" form an angle α with the axis 67 of the receiving chamber 72 in such a way that the opening of the "U" is toward the body 26 of the connector 16. This angle a is between 5° and 30°. The space 78 between the two hooks 72a, 72b is delimited by the faces 78a and 78b forming the sides of the hooks 72a and 72b, respectively. This space 78 penetrates into the receiving chamber 72 of the endless screw 20 by at least the depth of the threads 21 of said endless screw 20 without protruding on the hole 74. The opening of the space 78 is equal to the thickness of the pinion 18 which said space 78 receives.

Initially, the collar 24 is mounted in its seat 33 situated in the body 26 of the first connector 12 and the locking means 22 is engaged in the tapped upper part 31 of the orifice 30 and not locked, in order to give the collar 24 freedom of movement within its seat 33. The block 60 is engaged on the threaded end 62 of the rod 14 and the pinion 18 on the opposite end beyond the grip orifice 64.

The whole device is introduced into the patient's body via the access route prepared. The first connector 12 with its collar 24 and its locking means 22 is mounted on the head 6 of the first of the bicortical screws 2 in such a way that it is completely trapped in the collar 24 and such that the inner face 38 of said collar 24 is in contact with the outer face 10 of the head 6 of the bicortical screw 2 and the protruding lip 44 in contact with the flange 8 of the screw 2. The second connector 16 is then engaged completely on the head 6 of the second of the bicortical screws 2 via the hole 74. The lower face 80 of the connector 16 is in contact with the flange 8 of the screw 2. The rod 14 is then introduced, held via its grip orifice 64, then positioned at the bottom of the bifid hooks 28, 72 of the first connector 12 and second connector 16, respectively, in such a way that:

the block 60 is inserted in the space 52 of the first connector 12, and with one of its faces 61 in contact with the bearing face 58, the pinion 18 is inserted in the space 78 of the second connector 16, the teeth protruding inside the receiving chamber 72 for the endless screw 20.

The locking means 22 is then tightened. The face 36 of the collar 24 then slides on the lower face 48 of the locking means 22 and, by virtue of the presence of the slit 40 and of the groove 41, forces the collar 24 to close again, in other words to tighten on the head 6 of the bicortical screw 2, immobilizing the whole connector 12 in position on said screw 2. The endless screw 20 is then positioned in the receiving chamber 72 of the second connector 16, the threads 21 engaging with the teeth of the pinion 18. The device is then ready to effect distraction or contraction by rotation of the endless screw 20 within the receiving chamber 72 of the second connector 16.

Figure 5:
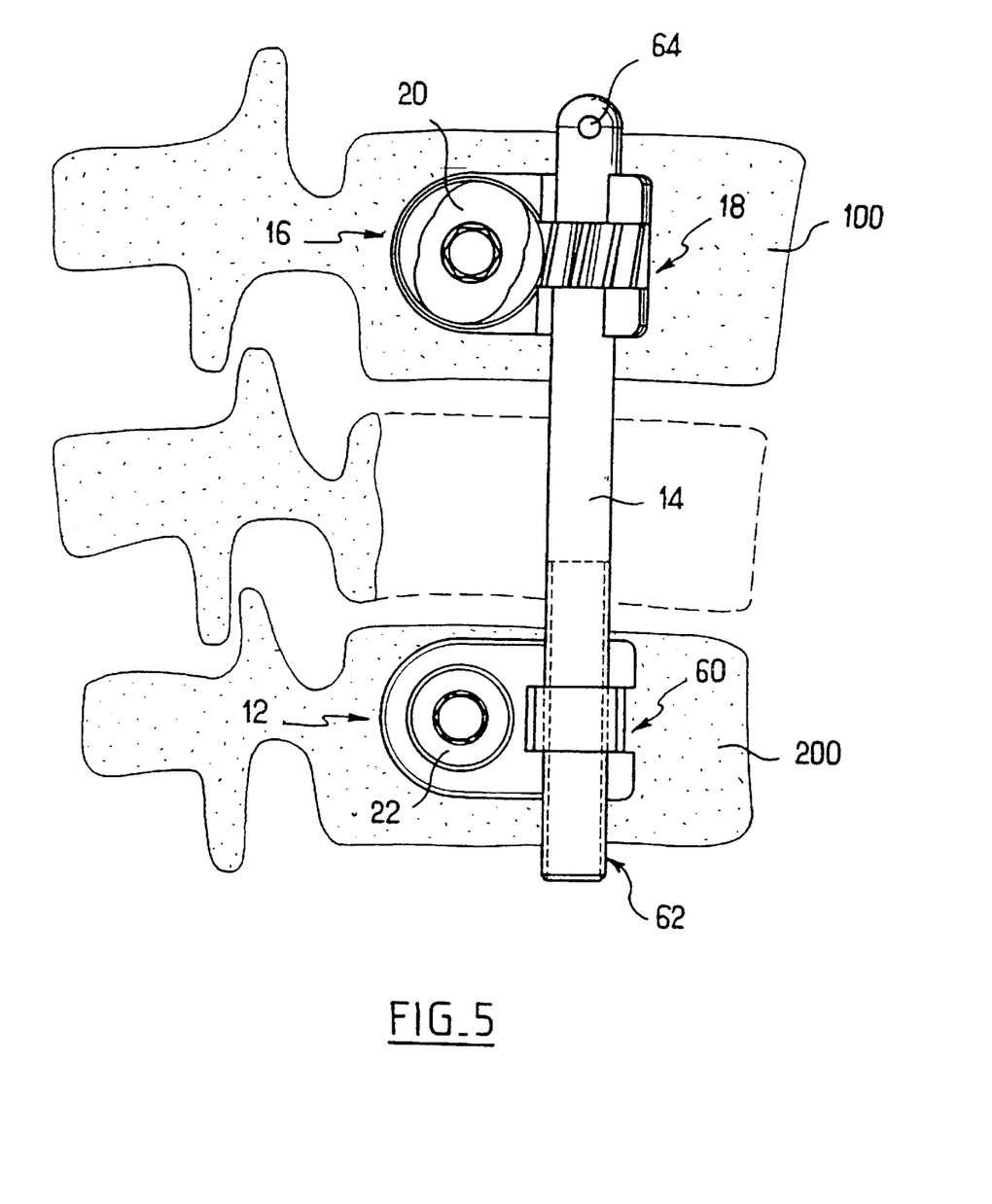
FIG. 5 is a plan view of the first embodiment placed on a vertebral column.

In the case of distraction, the rod 14 driven in rotation by the pinion 18, which is itself maneuvered by the endless screw 20, unscrews in the block 60. The latter bears against the face 52a of the first connector 12 while the pinion 18 bears on the face 78b of the second connector 16. The two connectors are forced to move away from one another, entraining the bicortical screws 2 and the vertebrae 100, 200 where the screws 2 are anchored.

In the case of contraction, the rod 14 driven in rotation by the pinion 18, maneuvered by the endless screw 20, screws in the block 60. The latter bears against the face 52b of the first connector while the pinion 18 bears on the face 78a of the second connector 16. The two connectors are forced to move toward one another, entraining the bicortical screws 2 and the vertebrae 100, 200 where the screws 2 are anchored.

During these movements the pinion 18 can neither be extracted nor extract the rod 14 on account of the angle a of the branches 74, 75 of the "U" of the receiving hook 72 of the second connector 16 which, via the rod 14, press the pinion 18 against the endless screw 20 without any possibility of escape.

Once the desired distance has been obtained, a spinal osteosynthesis system is placed between the vertebrae between these vertebrae such as, for example, intersomatic cages, then the device forming the subject of the present invention is removed from the patient's body via the access route prepared. Finally, arthrodesis is completed by fitting a second osteosynthesis system on the anchoring members, for example an anterior fixation device, which will ensure the stability of the spinal segment thus equipped during the fusion by means of the first osteosynthesis system.

Figure 6:
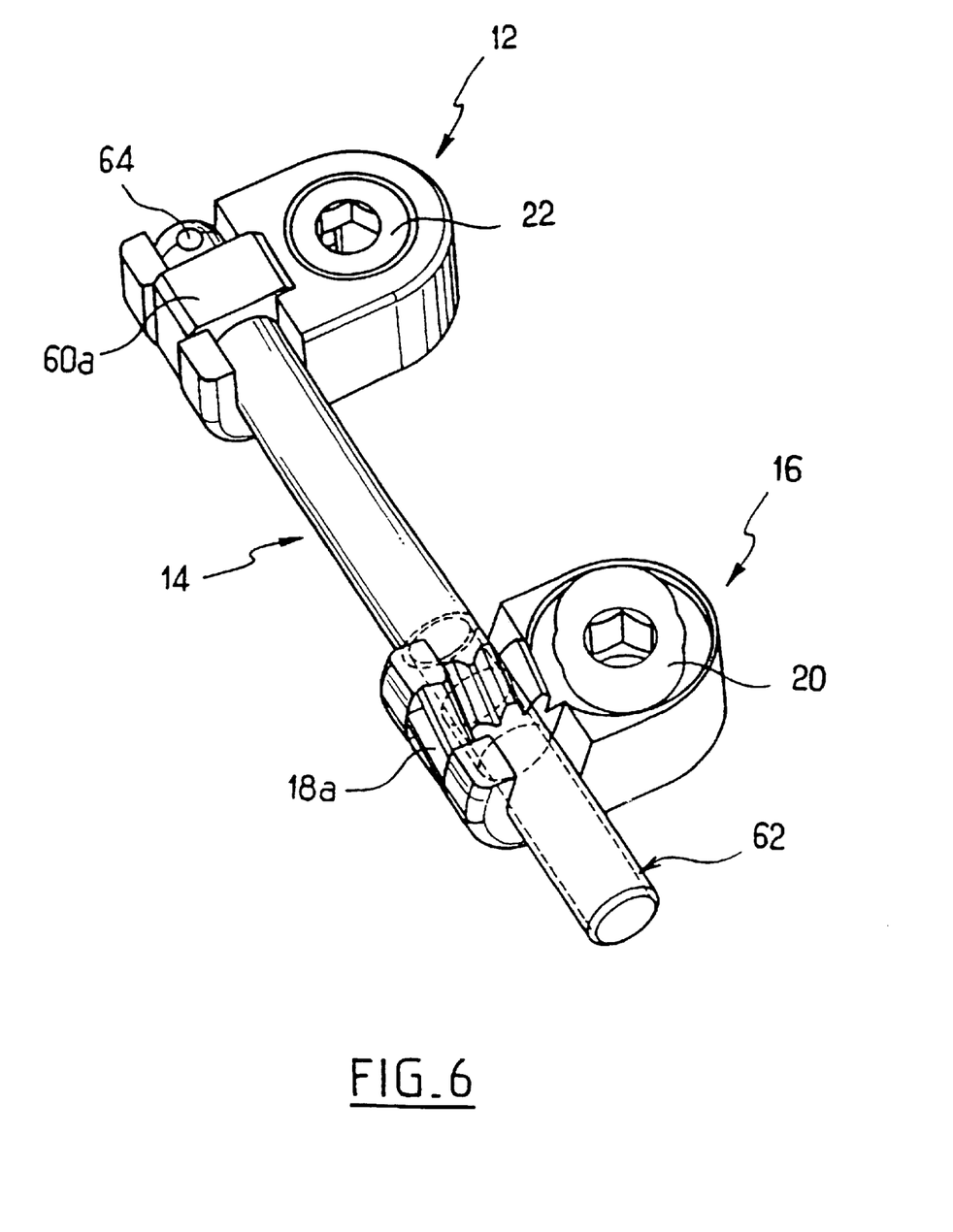
FIG. 6 is a view, in three dimensions, of a second embodiment.

The second embodiment is illustrated in FIG. 6. It differs from the first embodiment discussed above in that:

the block 60a is integral with the rod 14 immobilizing said rod 14 in rotation and in translation in the direction of its own axis relative to the first connector 12, the pinion 18a acts as a nut whose thread is in engagement with that 62 of the rod 14.

The first and second connectors 12, 16 are identical to those described in the first embodiment. These connectors 12, 16 and the rod 14 are also assembled in a similar way. During distraction or contraction, the rod 14 is immobile in rotation and it is the pinion 18a which, by screwing or unscrewing on the rod 14, effects the variations in distance between the two connectors 12, 16 of the device.

Figure 7A:
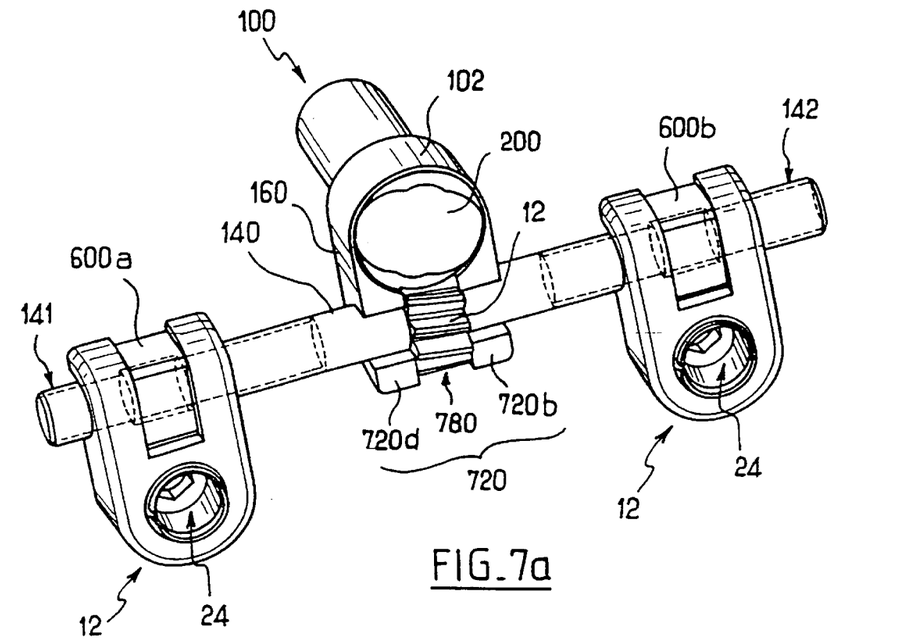
FIG. 7a is a bottom view of a third embodiment, in three dimensions.
Figure 7B:
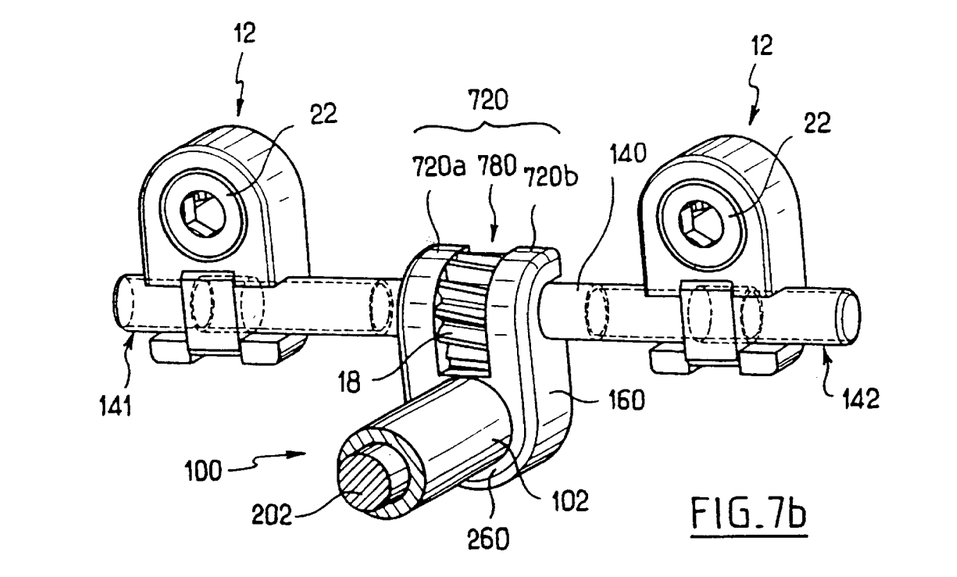
FIG. 7b is a plan view of the third embodiment, in three dimensions.

The third embodiment is illustrated in FIGS. 7a and 7b. The connectors placed on the heads 6 of bicortical screws 2 are identical to the first connector 12 described in the first embodiment discussed above. The pinion 18 is integral with the rod 140 and is situated at the middle of the rod 140. The ends of the rod 140 each comprise a thread 141, 142. The directions of these threads are opposite to each other. A block 600a, 600b having the complementary thread is engaged on each of these threads 141, 142. The system comprises a connector 160 situated at the end of a body 102 of instrument 100, similar to the second connector 16 described in the first embodiment discussed above, except as regards the direction of the branches of the "U" of the receiving hook 720 which are parallel to the axis of the receiving chamber. The body 102 of the instrument 100 is linked to the connector 160 in the area of its body 260. The system comprises an endless screw 200 integral with a drive means 202 passing through the body 102 of the instrument 100.

The connectors 12 are fitted as before. The rod 140 is then installed in the receiving hooks 28 of said connectors 12 in such a way that the blocks 600a, 600b are in the space 52 between the respective bifid receiving hooks 28, as described previously. The instrument 100 is then positioned on the rod 140 in the area of the pinion 18, the latter being placed in the space 780 of the bifid receiving hook 720 of the connector 160 of the instrument 100. The pinion 18 is in engagement with the threads of the endless screw 200.

During distraction, the rod 140, driven in rotation by the pinion 18, which is itself moved by the endless screw 20, unscrews simultaneously in the two blocks 600a, 600b which move away from one another, entraining the connectors 12 in distraction.

During contraction, the rod 140, driven in rotation by the pinion 18, which is moved by the endless screw 20, screws simultaneously in the two blocks 600a, 600b which move toward one another, entraining the connectors 12 in contraction.

Of course, numerous modifications may be made to the invention without departing from the scope thereof.

It will be possible to provide for the following:

the block is of a general polygonal cross section;

the block is of circular cross section;

the first connector comprises a threaded hole instead of the bifid receiving hook and the block;

the rod is integral with the first connector instead of the bifid hook and the block; or the second connector has a ball and socket link to its anchoring member.

The anchoring members can be pedicle screws or alternatively hooks.

In each of the above illustrative embodiments, the system will preferably be designed so as to be mechanically irreversible as regards the meshing between the components. Thus, in the first embodiment, the endless screw 20 is actuated so as to displace the vertebral anchoring members. But no stress on the latter can in return move the components, in particular the endless screw, in the opposite direction. The same applies to the second embodiment. In the third embodiment, the drive means 202 makes it possible to displace the two vertebral anchoring members, but not the opposite way. The conditions for obtaining such irreversibility are known per se in other fields. Irreversibility depends in particular on the inclination of the teeth and the threads of the meshing components.

What is claimed is:

1. A device for use in surgery of the spine, comprising at least two connectors to be fixed to a respective vertebral anchoring members, means for linking said connectors, and means for adjusting a distance between said connectors, the adjustment means comprise an assembly of a pinion and an endless screw, said connectors including a recess adapted for receiving said means for linking said connectors, wherein said linking means is placed into said recess by moving said linking means in an anterior direction toward a vertebral body after said anchoring members have been engaged with the vertebral body.

2. The device as claimed in claim 1, wherein said means for adjustment of said distance of said connectors comprise a rod designed to link said connectors.

3. The device as claimed in claim 2, wherein said rod is free to translate and rotate on its own axis relative to a first connector.

4. The device as claimed in claim 3, wherein said rod is free to rotate about its own axis relative to a second connector.

5. The device as claimed in claim 3, wherein said rod is free to translate and rotate about its own axis relative to said second connector with a helix of opposite direction.

6. The device as claimed in claim 3, 4, or 5, wherein a pinion is rigidly fixed to said rod.

7. The device as claimed in claim 2, wherein said rod is immobilized in translation and in rotation on its own axis relative to a first connector.

8. The device as claimed in claim 7, wherein said rod is free in translation on its own axis relative to a second connector.

9. The device as claimed in claim 7 or 8, wherein said pinion forms a screw/nut link with said rod.

10. The device as claimed in claim 2, wherein said pinion links said rod and at least one connector.

11. The device as claimed in claim 10, wherein at least one of said connectors has a bifid hook deliminating a space designed to receive said rod and said pinion.

12. The device as claimed in claim 2, further comprising a linking means between said rod and at least one connector, said linking means comprising a block which forms an abutment for the translation and/or rotation movement of said rod relative to said connector on the axis of said rod.

13. The device as claimed in claim 12, wherein said block has a polygonal cross section.

14. The device as claimed in claim 13, wherein said block has four sides.

15. The device as claimed in claim 13, wherein said connector has a bifid hook having a space for receiving said block.

16. The device as claimed in claim 15, wherein said block is received, one of the sides of the polygonal cross section of said abutment is able to come into contact with the bottom of said space of said bifid hook.

17. The device as claimed in claim 2, further comprising a coupling for engaging and rotating said endless screw.

18. The device as claimed in claim 17, wherein said coupling comprises a hook having two prongs spaced to receive said pinion rigidly integral with said rod with a hook portion of said two prongs for receiving said rod.

19. The device as claimed in claim 1, further comprising a ring with a spherical face.

20. The device as claimed in claim 19, wherein said connector comprises a chamber designed to receive said ring with rotation.

21. The device as claimed in claim 19 or 20, wherein said connector comprises a locking means designed to immobilize said ring in rotation.

22. The device as claimed in claim 21, wherein said locking means comprises a concave spherical face for contacting said spherical face of said ring.

23. The device as claimed in claim 19, wherein said ring is designed to be fitted on said vertebral anchoring member.

24. The device as claimed in claim 2, wherein one of said connectors is adjacent to said pinion and said endless screw assembly.

25. The device as claimed in claim 24, wherein said endless screw is designed to be rotatably received within said connector.

26. The device as claimed in claim 1 in that one of said connectors forms a ball and socket link with the associated vertebral anchoring member.

27. A device for moving two vertebra towards or away from one another comprising:
first and second anchoring elements for engaging a respective first and second vertebra of the two vertebra;
a first and second connector respectively coupled to said first and second anchoring elements, at least one of said connectors having a drive element thereon and said other connector having a recess;
a rod extending between and engaging said first and second connectors, said rod having a drive element integral therewith engaging said drive element on said at least one connector so that the interaction of said drive elements causes the movement of said two vertebra towards or away from one another, wherein said rod is received by said recess by moving said rod in an anterior direction toward the two vertebra after said anchoring elements have engaged the two vertebra.

28. The device as set forth in claim 27, wherein said anchor elements are bone screws.

29. The device as set forth in claim 28, wherein said connector element engages a head on said anchoring elements and has a support surface for supporting said rod.

30. The device as set forth in claim 27, wherein said rod includes a pinion integrally mounted thereon.

31. The device as set forth in claim 30, further including a drive screw for engaging said pinion and causing rotation of said rod about a longitudinal axis thereof.

32. The device as set forth in claim 27, wherein said first and second connectors each have drive elements therein engaging a pair of drive elements on said rod.

33. The device as set forth in claim 32, wherein said rod further includes a pinion integral therewith located in intermediate first and second drive elements thereon.

34. The device as claimed in claim 33 further including a drive screw for engaging said pinion for rotating said rod about a longitudinal axis thereof.

35. A spinal distraction device comprising a first connector for engaging a first vertebrae, said first connector having a rotary drive element thereon;
a second connector for engaging a second vertebra, said second connector having a threaded bore and a recess;
a rod extending between said first and second connectors along a longitudinal axis, said rod having a rotary drive element thereon engaging said rotary drive element on said first connector and a first threaded portion engaging said bore in said second connector, wherein said rod is received by said recess by moving said rod in an anterior direction toward the two vertebra after said anchoring elements have engaged the two vertebra; and
means for rotating said rod to move at least one of said first and second connectors with respect to said rod.

36. The distraction device as set forth in claim 35, wherein said rotary drive element on said first connector is a threaded bore.

37. The distraction device as set forth in claim 36, wherein said rod has a second threaded portion engaging said threaded bore in said first connector and said means for rotating said rod includes a drive element mounted on said rod intermediate with said first and second drive elements.

38. A device for use in surgery of the spine, comprising at least two connectors to be fixed to respective vertebral anchoring members, means for linking these connectors, and means for adjusting a distance between these connectors, said adjustment means comprising an assembly of a pinion and an endless screw, and linking means between said rod and at least one connector, said linking means comprising a block which forms an abutment for the translation and/or rotation movement of said rod relative to said connector on said axis of said rod.

39. The device as claimed in claim 38, wherein said block has a polygonal cross section.

40. The device as claimed in claim 39, wherein said block has four sides.

41. The device as claimed in claim 39, wherein said connector has a bifid hook having a space for receiving said block.

42. The device as claimed in claim 41, wherein said block is received, one of the sides of the polygonal cross section of said abutment is able to come into contact with the bottom of said space of said bifid hook.

43. The device as claimed in claim 39, wherein one of said connectors comprises a ring with a spherical face, wherein said connector comprises a chamber designed to receive said ring with rotation, and a locking means to immobilize said ring in rotation.

44. The device as claimed in claim 43, wherein said locking means comprises a concave spherical face for contacting said spherical face of said ring.

45. The device as claimed in claim 38, wherein at least one of said connectors has a bifid hook deliminating a space designed to receive said rod and said pinion.

46. The device as claimed in claim 38, wherein said means for adjustment of said distance of said connectors comprises a rod designed to link said connectors, further comprising a coupling for engaging and rotating said endless screw, wherein said coupling comprising a hook having two prongs spaced to receive said pinion rigidly integral with said rod with a hook portion of said two prongs for receiving said rod.

* * * * *

UNITED STATES PATENT AND TRADEMARK OFFICE
CERTIFICATE OF CORRECTION

PATENT NO. : 6,749,613 B1
DATED : June 15, 2004
INVENTOR(S) : Frédéric Conchy and Denis Pasquet It is certified that error appears in the above-identified patent and that said Letters Patent is hereby corrected as shown below:

Column 4,
Line 42, "a" should read -- $\alpha$ --.

Column 5,
Line 40, "a" should read -- $\alpha$ --

Column 7
Line 3, delete "a".
Line 52, after the word "wherein" insert the word -- when --.

Column 8,
Line 48, after the number "33" add a comma -- , --.

Column 9,
Line 23, after the word "wherein" insert the word -- when --.

Column 10,
Line 18, delete the word "comprising" and in place thereof insert the word -- includes --.

Signed and Sealed this

Twenty-eighth Day of September, 2004

JON W. DUDAS
*Director of the United States Patent and Trademark Office*